US008200003B2

(12) United States Patent
Michelsson

(10) Patent No.: US 8,200,003 B2
(45) Date of Patent: Jun. 12, 2012

(54) METHOD FOR THE OPTICAL INSPECTION AND VISUALIZATION OF OPTICAL MEASURING VALUES OBTAINED FROM DISK-LIKE OBJECTS

(75) Inventor: Detlef Michelsson, Wetzlar-Naunheim (DE)

(73) Assignee: Vistec Semiconductor Systems GmbH, Weilburg (DE)

( * ) Notice: Subject to any disclaimer, the term of this patent is extended or adjusted under 35 U.S.C. 154(b) by 875 days.

(21) Appl. No.: 12/228,582

(22) Filed: Aug. 14, 2008

(65) Prior Publication Data
US 2009/0052766 A1 Feb. 26, 2009

(30) Foreign Application Priority Data

Aug. 23, 2007 (DE) .......................... 10 2007 039 982

(51) Int. Cl.
*G06K 9/00* (2006.01)
(52) U.S. Cl. ........................................ 382/145; 382/141
(58) Field of Classification Search ........... 382/141–152
See application file for complete search history.

(56) References Cited

U.S. PATENT DOCUMENTS

| 5,875,108 | A * | 2/1999 | Hoffberg et al. ................. 700/17 |
| 6,067,153 | A * | 5/2000 | Mizuno ....................... 356/237.2 |
| 6,252,242 | B1 * | 6/2001 | Brunfeld et al. ......... 250/559.45 |
| 6,272,248 | B1 * | 8/2001 | Saitoh et al. ................... 382/218 |
| 6,292,582 | B1 * | 9/2001 | Lin et al. ......................... 382/149 |
| 6,947,587 | B1 * | 9/2005 | Maeda et al. .................. 382/149 |
| 7,065,460 | B2 * | 6/2006 | Nishimura ....................... 702/81 |
| 7,557,963 | B2 * | 7/2009 | Bhattacharjya .............. 358/3.27 |
| 7,873,215 | B2 * | 1/2011 | Xiao et al. ...................... 382/173 |
| 2002/0195574 | A1 * | 12/2002 | Tanaka et al. .............. 250/492.3 |
| 2003/0007677 | A1 * | 1/2003 | Hiroi et al. .................... 382/149 |
| 2004/0027618 | A1 * | 2/2004 | Nakamura et al. ........... 358/3.26 |
| 2005/0196040 | A1 * | 9/2005 | Ohara ........................... 382/167 |
| 2006/0176476 | A1 | 8/2006 | Michelsson ................ 356/237.2 |
| 2006/0240580 | A1 | 10/2006 | Michelsson ..................... 438/14 |
| 2007/0076943 | A1 | 4/2007 | Wienecke et al. ............ 382/145 |

FOREIGN PATENT DOCUMENTS

| DE | 10 307 454 | 9/2004 |
| DE | 103 31 686 | 2/2005 |
| DE | 10 2005 017 642 | 10/2006 |
| EP | 1 712 898 | 10/2006 |

* cited by examiner

*Primary Examiner* — Gregory J Toatley
*Assistant Examiner* — Jarreas C Underwood
(74) *Attorney, Agent, or Firm* — Davidson, Davidson & Kappel, LLC

(57) ABSTRACT

The present invention relates to a method for optically inspecting and visualizing optical measuring values from at least one image of a disk-like object, including the steps of recording said at least one image of said at least one disk-like object, wherein a plurality of optical measuring values are produced from said at least one recorded image; generating a resulting image, wherein an area of the surface of said disk-like object having optical measuring values within a predetermined interval, is associated with a color or brightness value selected from a predetermined range; and varying at least one imaging parameter as a function of the detected and evaluated optical measuring values and/or as a function of a visual inspection of the resulting image by an operator.

14 Claims, 4 Drawing Sheets

METHOD FOR THE OPTICAL INSPECTION AND VISUALIZATION OF OPTICAL MEASURING VALUES OBTAINED FROM DISK-LIKE OBJECTS

This claims the benefit of German Patent Application No. 10 2007 039 982.2, filed on Aug. 23, 2007 and hereby incorporated by reference herein.

The present invention relates to a method for the optical inspection and visualization of optical measuring values obtained from disk-like objects.

BACKGROUND

In the production of semiconductors, during the manufacturing process, wafers are sequentially processed in a plurality of process steps. As integration densities increase, the requirements as to the quality of the structures formed on the wafer become ever more demanding. To be able to verify the quality of the structures formed and to find any defects, the requirements as to the quality, the precision and the reproducibility of the components and process steps for handling the wafer are correspondingly stringent. This means that in the production of a wafer including a great number of process steps and with a great number of layers of photoresist to be applied, the reliability and early detection of defects is particularly important. In the optical detection of defects, it is a question of taking into account systematic defects due to thickness variations in the application of photoresist on the semiconductor wafer, so as to avoid marking positions on the semiconductor wafer that do not include a defect.

By means of a so called macro inspection, semiconductor surfaces are optically scanned to detect defects. In this way, for example, wafer surfaces are scanned. The detected defects are visually shown on a wafer overview image. In some of the continuous processing steps the resulting overview images are very weak in contrast, so that the defects can often only be detected with difficulty. However, algorithms are known with the help of which defects can be found and identified as such, which cannot be reliably detected with the human eye and identified as a defect. Since automatically detected defects, or defects detected by means of suitable algorithms must be checked by a so-called operator and confirmed as a defect, if any, it is desirable to improve the imaging quality of the detected defects.

German Patent Application DE 10 307 454 A1 discloses a method, an apparatus and a software for the optical inspection of the surface of a semiconductor substrate, and a method and an apparatus for manufacturing a structured semiconductor substrate with the use of such a method or such an apparatus. In the method, for optical inspection an image is recorded of the surface of a semiconductor substrate. The image consists of a plurality of image points (pixels), each having at least three associated intensities of different wavelengths, which are referred to as color values. From the color values, by means of a transformation into a color space, which is defined by an intensity and by color coordinate values, a frequency distribution of image points having the same color coordinates is calculated. The thus calculated frequency distribution is used for a comparison with a second correspondingly calculated frequency distribution or a quantity derived therefrom. This method does not enable a visual comparison or a visual evaluation of a disk-like substrate.

Macroscopic images of semiconductor wafers show that the homogeneity of the layers changes radially. In particular in the application of photoresist there are varying homogeneities in the areas remote from the center point of the wafer. If a uniform sensitivity is used across the entire radius of the wafer, as has hitherto been the case for evaluating images of the imaged wafers, deviations near the edge may always be detected, while defects in the interior (close to the center point of the wafer) are not detected. If a high sensitivity is selected in order to reliably detect defects in homogeneous areas, erroneous detections increase in the edge regions, since the inhomogeneous edge regions are not always to be evaluated as defects. In order to avoid this, the edge regions can be completely omitted. This means, however, that no real defects are found there. If a reduced sensitivity is chosen, however, there are no more erroneous detections, but defects in the homogeneous areas cannot be found.

German Patent Application DE 103 31 686.8 A1 discloses a method for evaluating recorded images of wafers or other disk-like objects. The recording of the image of at least one reference wafer is followed by obtaining and visualizing the radial distribution of the measuring values of the reference wafer as a radial homogeneity function on a user interface. A sensitivity profile as a function of the radius is changed while taking the measured radial homogeneity function of the reference wafer into account. At least one parameter of the sensitivity profile is varied, allowing a trained sensitivity profile to be visually determined from the comparison with the radial homogeneity function. This method, again, does not show an image of the entire wafer with the aid of which the image or the images are then evaluated with respect to defects.

U.S. Pat. No. 7,065,460 discloses an apparatus and a method for inspecting semiconductor components. The apparatus is for inspecting the electrical characteristics of the semiconductor product. The measuring values obtained from the inspection are associated with various colors for visualization on a display.

The illustrative display of measuring values in the form of graphs in diagrams only makes sense for one dimension of the distribution of measuring points. If the measuring points are distributed in space, they must be reduced to one dimension in a visual image. This involves a loss of information. A visualization in a 3-D plot does not always lead to an illustrative image, since some points may be covered by others. It is very difficult to establish a link between the initial information and the measuring values. The representation in the form of numbers does not allow conclusions to be drawn as to the spatial distribution of the measuring values.

To improve the imaging quality of the optically detected wafer surfaces, image processing methods have been known for some time with the aid of which the resulting images can be processed to facilitate subsequent evaluation and to make the process of decision finding by an operator more reliable and less prone to error. However, subsequent image processing methods slow down the processing and inspection speed since image recording and image processing are separated on a temporal and sometimes on a local basis. For this reason a rapid evaluation of the recorded images is often not possible. If, for example, wafer surfaces have been found which make a further processing of the wafer in question appear at least partially doubtful, it may happen that the production process must be interrupted to wait for the subsequent evaluation of the images. The establishment and optimization of recipes is thus made difficult.

SUMMARY OF THE INVENTION

It is an object of the present invention to provide an improved method for optical inspection and defect detection which allows for speedy defect detection with the same high reliability in the defect detection.

This object is achieved according to an embodiment of the present invention by a method for optically inspecting and visualizing optical measuring values from at least one image of a disk-like object, including the following steps: First, at least one image of the at least one disk-like object is recorded, wherein a plurality of optical measuring values are produced from the at least one recorded image. Then a resulting image is generated, wherein one area of the surface of the disk-like object, having measuring values which lie within a predetermined interval, is associated with a color or brightness value selected from a predetermined range. Finally, at least one imaging parameter is varied as a function of the detected and evaluated optical measuring values and/or as a function of a visual inspection of the resulting image by an operator.

These imaging parameters can be, for example, a contrast, a brightness, a gamma correction, a colour balance and/or a colour saturation of the resulting image. At least one of the parameters can be varied manually or by a computer program automatically. Optionally, several or all parameters can be varied manually or by a computer program automatically.

The desired or suitable modification of the image data can be adjusted in advance by the operator in question or can be automatically selected. Various parameters can be defined, for example, by a line engineer, allowing the critical defects of the process step under inspection to be optimally visualized. These parameters can be, in particular, the contrast, the brightness, the gamma correction, the colour balance and the colour saturation. The operator can vary the resulting image with the help of this parameter set in such a way that a visual evaluation can be made better and more reliable.

One embodiment of the present invention provides that the recorded image of the disk-like substrate and the resulting image can be shown on a display of a system for optically inspecting a disk-like substrate, wherein for the evaluation of defects on the disk-like substrate, a switchover can be made between the recorded image of the disk-like substrate and the resulting image. The selection of the parameters for image variation is at the discretion of the user. Further, it is advantageous to provide for a switchover between an unmodified and a modified view with varied imaging parameters. In this way it is possible for the user to individually adjust the parameters for image variation according to the requirements and the detectability of the defect locations to be detected.

One embodiment of the present invention provides that the disk-like object is placed on a stage, wherein the stage is traversable in a first direction X and a second direction Y, that an imaging means is provided, wherein an image field of the imaging means is smaller than the entire surface of the disk-like substrate and that for recording the entire surface of the disk-like substrate the imaging means scans the disk-like substrate in a meandering fashion.

Preferably, the resulting image has the same form as the recorded image of the disk-like object. The disk-like object can be a flat panel display, in particular. The disk-like object is typically a wafer or another semiconductor element.

The processing of the image as shown does not, however, improve the signal-to-noise ratio. This is why processing should not be carried out prior to the actual defect detection. The processing of the image may lead, however, to the range of values being exceeded, i.e. to a saturation of certain image areas, which may be acceptable, however, in the context of the visual evaluation of defect locations.

To enable an evaluation of the original image, preferably, there can always be a switchover between the original view and the processed view. This allows image areas to be evaluated which appear saturated and therefore less distinct after processing. The original image remains unchanged.

BRIEF DESCRIPTION OF THE DRAWINGS

Exemplary embodiments of the present invention and their advantages will be explained in the following with reference to the accompanying drawings in more detail, wherein.

DETAILED DESCRIPTION

Figure 1:
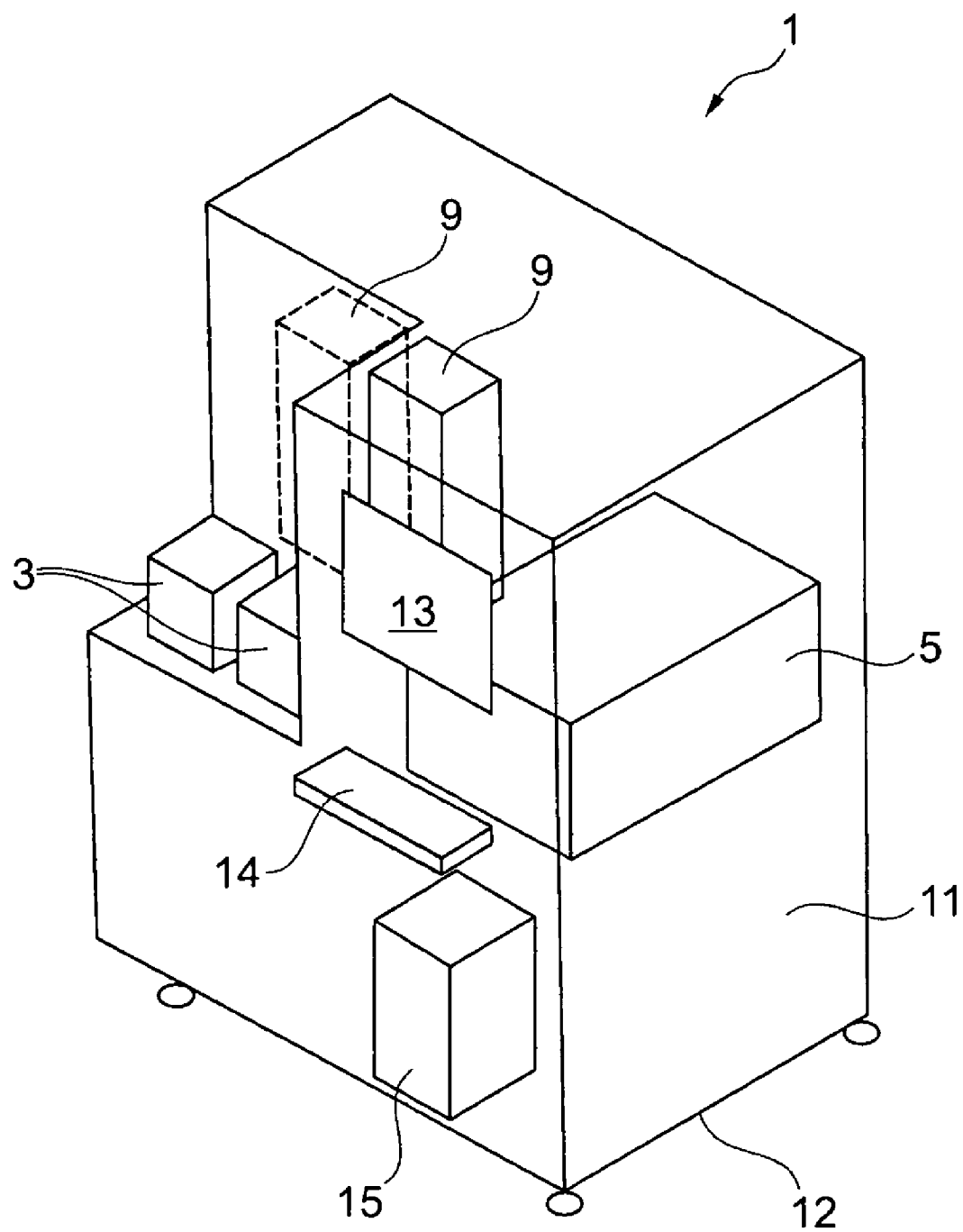
FIG. 1 is a schematic representation of a system for detecting defects on wafers or disk-like substrates.

The diagrammatic view of FIG. 1 shows a system 1 for detecting defects on wafers. System 1 is comprised, for example, of at least one cartridge element 3 for the semiconductor substrates or wafers. In a measuring unit 5, images or image data of individual wafers are recorded. Between cartridge element 3 for the semiconductor substrates or wafers and measuring unit 5, a transport mechanism 9 is provided. System 1 is enclosed by a housing 11, wherein housing 11 defines a base area 12. In system 1, a computer 15 is further integrated for recording and processing the images or image data from the individually measured wafers. System 1 is also equipped with a display 13 and a keyboard 14. The user can use keyboard 14 for inputting data for controlling the system or also for inputting parameters for evaluating the image data of individual wafers. Display 13 is for showing the user of the system a plurality of user interfaces.

Figure 2A:
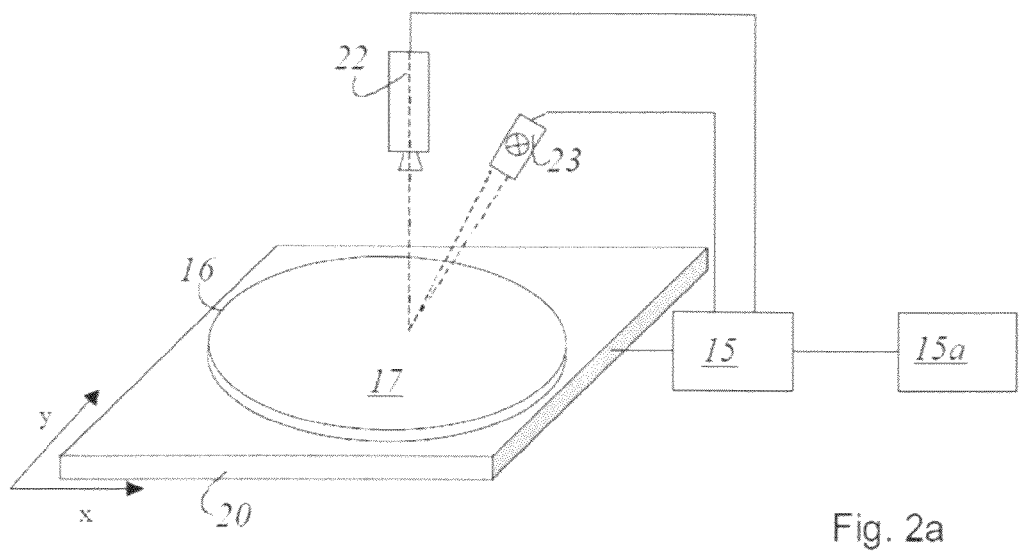
FIG. 2a is a diagram of the way in which the images or image data of a wafer are recorded.

FIG. 2a is a schematic view of the way in which images and/or image data are detected from a wafer 16. Wafer 16 is placed on a stage 20 traversable within housing 11 in a first direction X and a second direction Y. The first and second directions X, Y are perpendicular to each other. An imaging means 22 is provided above surface 17 of wafer 16, wherein the image field of imaging means 22 is smaller than the entire surface 17 of wafer 16. In order to scan the entire surface 17 of wafer 16 with imaging means 22, wafer 16 is scanned in a meandering fashion. The individually sequentially detected image fields are then combined to result in an overall image of surface 17 of wafer 16. This is also done by computer 15 provided within housing 11. To generate a relative movement between stage 20 and imaging means 22, an X/Y scanning stage is used in the present embodiment, which can be traversed in the X and Y coordinate directions. Camera 23 is fixedly installed with respect to stage 20. The reverse can of course also be the case, where stage 2 is fixedly installed and imaging means 22 can be moved across wafer 16 for imaging. A combination of traversing the camera 23 in one direction and stage 20 in a direction perpendicular thereto is also possible.

Wafer 16 is illuminated by means of an illuminating means 23 for illuminating at least those areas of wafer 16, which correspond to the image field of imaging means 22. By means of the concentrated illumination which can also be pulsed by means of a flash lamp, imaging on-the-fly is possible, wherein stage 20 or imaging means 22 can be continuously traversed for imaging. This enables great wafer throughput. It is of course also possible to stop the relative movement between stage 20 and imaging means 22 for each image and to illuminate wafer 16 across its entire surface 17. Stage 20, imaging means 22 and illumination means 23 are controlled by computer 15. The images can be stored in a memory 15a by computer 15 and retrieved from there if necessary.

Figure 2B:
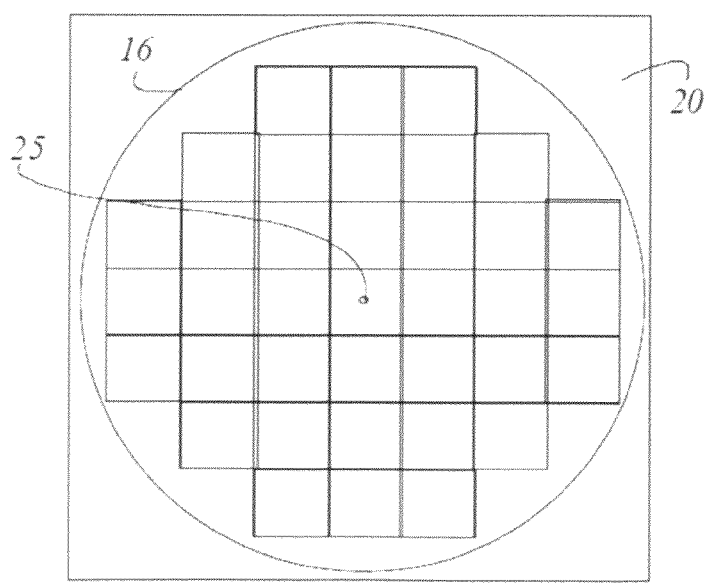
FIG. 2b is a top view of a wafer.

FIG. 2b is a top view of a wafer 16 placed on a stage 20. Wafer 16 has a centerpoint 25. Layers are deposited on wafer 16 which are then structured by means of further process steps. A structured wafer includes a plurality of structured elements.

Figure 3:
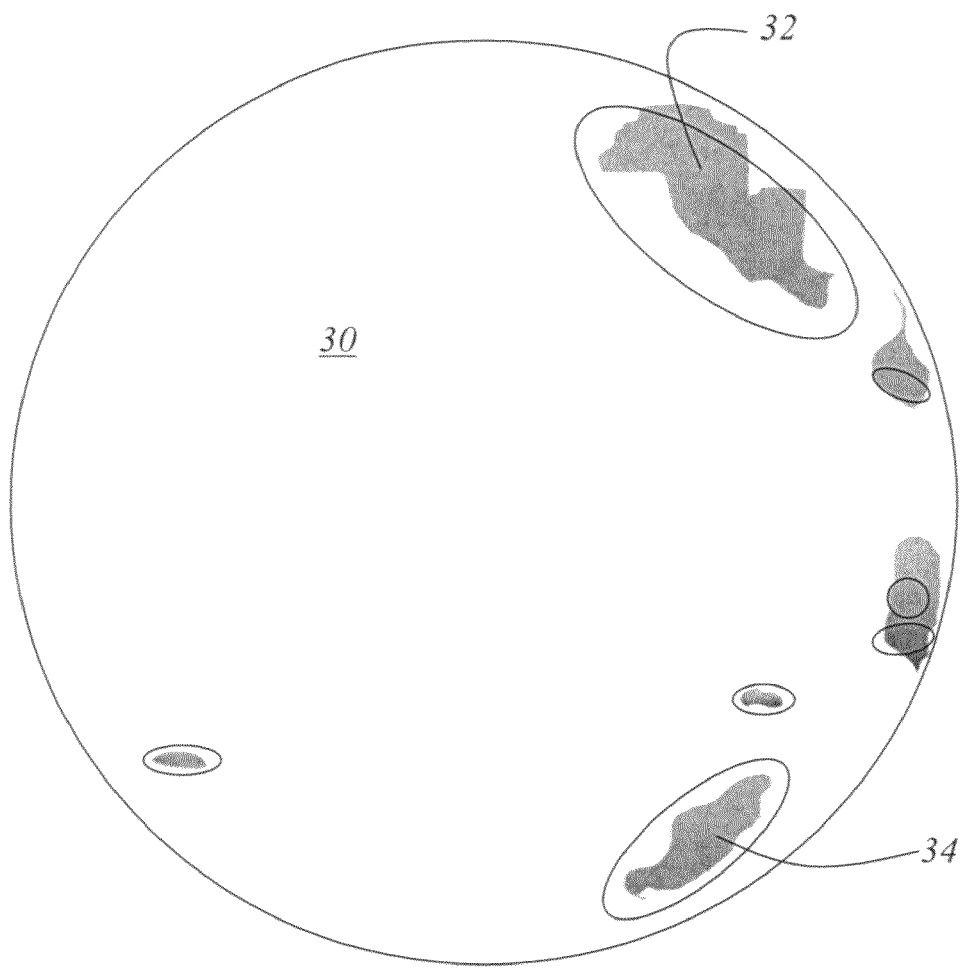
FIG. 3 shows a screen representation of an optically detected wafer surface without contrast enhancement.

FIG. 3 is a screen view of a wafer surface 30 including a plurality of defect locations 32 and 34, each marked with an elliptical line. In the present context, only the two larger defect locations 32 at the top right-hand edge of the round wafer surface 30, and 34 at the bottom right-hand edge, should be regarded. The smaller defect locations in the middle of the right edge area will not be closely scrutinized, even though the method according to the present invention can also improve the visibility of these defect locations. While the upper 32 of the two larger defect locations may have good visibility in the shown representation and may be accessible for further evaluation without problems, the magnitude and extension of the bottom defect location 34 may appear doubtful to the viewer and/or the image processing program used. With the bottom defect location 34 which is only weakly discernible, it may be necessary to stop wafer processing to unequivocally determine the extension and presence of the defect location, since otherwise there is a risk that the defective areas are exposed and undergo further processing steps and are discarded as defective at too late a point.

Figure 4:
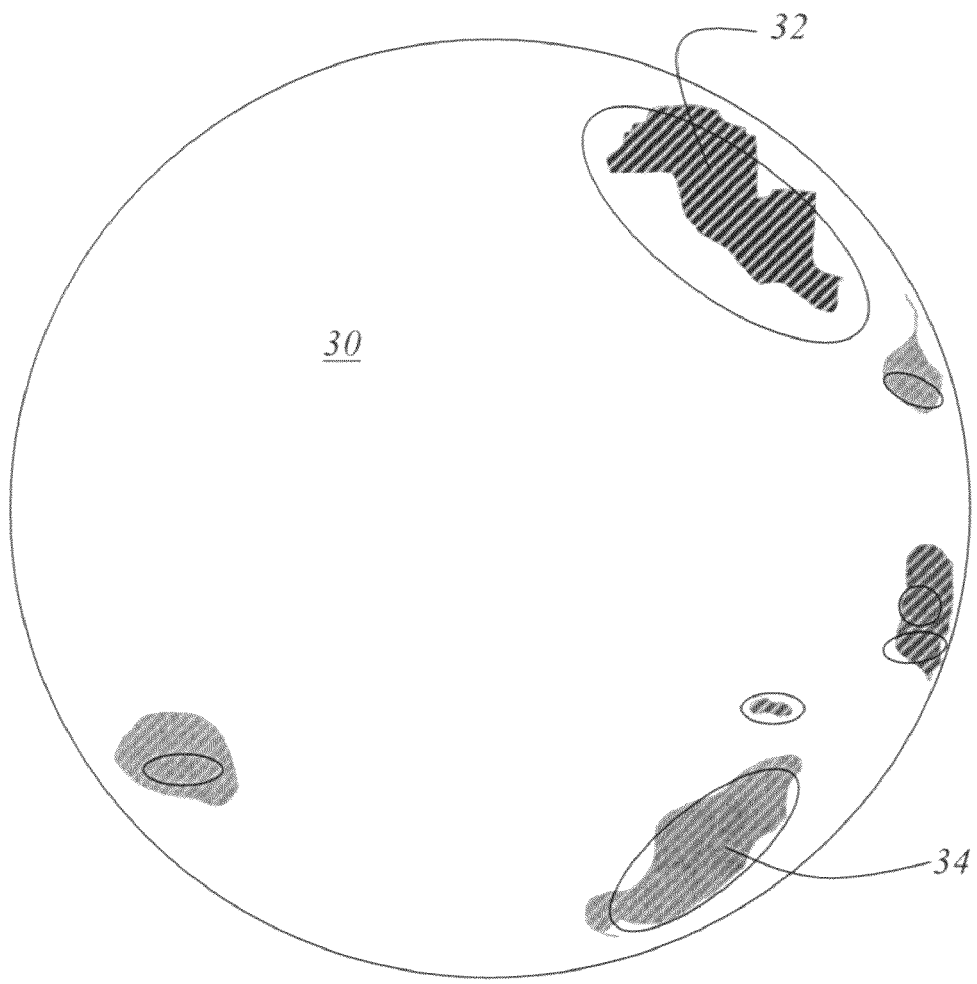
FIG. 4 shows a screen representation of the wafer surface according to FIG. 1 but with contrast enhancement.

The screen view of FIG. 4 illustrates an image of wafer surface 30, wherein defective locations 32, 34 are highlighted by means of contrast enhancement. While the top defect location 32 at the top right hand wafer edge is even more pronounced, the lower defect location 34 at the bottom right hand wafer edge is distinct only now, so that the presence and the extension of defect location 34 can now be unequivocally determined.

The improved screen view shown in FIG. 4 of defect locations 32 and 34 on wafer surface 30 can optionally also be obtained by means of other modifications to the image data which are either adjusted in advance by the operator in question or automatically selected. Various parameters can thus be defined by a line engineer allowing the critical defects of a processing step under inspection to be made optimally visible. These parameters can be, in particular, the contrast, the brightness, the gamma correction, the color balance and the color saturation. With the aid of this parameter set, the operator can modify the resulting image in such a way that the image can be better and more reliably visually evaluated.

The processing of the image shown does not improve, however, the signal-to-noise ratio. This is why the processing should not be carried out prior to the actual defect detection. The processing of the image may, however, lead to a value range being exceeded, i.e. to a saturation of certain image areas, which may be acceptable, however, in the context of the visual evaluation of the defect locations.

To facilitate the evaluation of the original image, it is preferably always possible to switch over between the original representation and the processed view. Thus image areas can also be evaluated which have been saturated by the processing and are therefore less distinct. This does not change the original image.

What is claimed is:

1. A method for optically inspecting and visualizing optical measuring values from at least one image of a disk-like object, comprising:
    recording said at least one image of said at least one disk-like object, wherein a plurality of optical measuring values are produced from said at least one recorded image;
    generating a resulting image, wherein an area of the surface of said disk-like object having optical measuring values within a predetermined interval, is associated with a colour or brightness value selected from a predetermined range; and
    varying one or more imaging parameters of the resulting image based on at least one of the detected and evaluated optical measuring values and a visual inspection of the resulting image by an operator to allow defects on the disk-like object to be optimally visible.

2. The method according to claim 1, wherein the one or more parameters consist essentially of contrast, brightness, gamma correction, colour balance and/or colour saturation of the resulting image.

3. The method according to claim 1, wherein at least one of said imaging parameters are varied manually or by a computer program.

4. The method according to claim 1, wherein a plurality of the imaging parameters are varied manually or by a computer program.

5. The method according to claim 4, wherein all of the imaging parameters are varied manually or by a computer program.

6. The method according to claim 1, wherein the recorded image of the disk-like substrate and the resulting image are shown on a display of a system for optically inspecting a disk-like substrate, and wherein for evaluating defects on the disk-like substrate a switchover can be made between the recorded image of the disk-like substrate and the resulting image.

7. The method according to claim 1, wherein a switchover can be made between an unmodified and a modified view with varied imaging parameters.

8. The method according to claim 1, wherein the disk-like object is placed on a stage, wherein the stage is traversable in a first direction X and a second direction Y, in that an imaging means is provided, wherein an image field of the imaging means is smaller than the entire surface of the disk-like object, and in that for imaging the entire surface of the disk-like substrate the disk-like substrate is scanned by the imaging means in a meandering fashion.

9. The method according to claim 1, wherein the resulting image has the same form as the recorded image of the disk-like object.

10. The method according to claim 1, wherein the disk-like object is a flat panel display.

11. The method according to claim 1, wherein the disk-like object is a wafer.

12. The method according to claim 1, wherein the area of the surface of said disk-like object having optical measuring values within the predetermined interval are defects.

13. The method according to claim 1, wherein varying step includes enhancing the one or more imaging parameters of the resulting image to highlight defects on the surface of the disk-like object.

14. A method for optically inspecting and visualizing optical measuring values from at least one image of a disk-like object, comprising:
    recording said at least one image of said at least one disk-like object;
    generating a resulting image of the disk-like object from said at least one recorded image such that areas of the surface of said disk-like object having optical measuring values within a predetermined interval are displayed in the resulting image as defect locations having predetermined colour or brightness values; and
    modifying image data of the resulting image by enhancing one or more imaging parameters to highlight the defect locations on the resulting image.

* * * * *